(12) United States Patent
Bluecher et al.

(10) Patent No.: US 10,675,297 B2
(45) Date of Patent: *Jun. 9, 2020

(54) COPOLYMERS OF HYDROPHOBIC AND HYDROPHILIC SEGMENTS THAT REDUCE PROTEIN ADSORPTION

(71) Applicant: BVW Holding AG, Cham (CH)

(72) Inventors: Lukas Bluecher, Eurasburg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/656,134

(22) Filed: Oct. 17, 2019

(65) Prior Publication Data

US 2020/0113933 A1  Apr. 16, 2020

Related U.S. Application Data

(63) Continuation of application No. 13/645,941, filed on Oct. 5, 2012, now Pat. No. 10,485,822.

(Continued)

(51) Int. Cl.
*A61K 31/785* (2006.01)
*C08G 18/66* (2006.01)
*C08G 18/64* (2006.01)
*C08G 18/42* (2006.01)
*C08G 18/75* (2006.01)
*C08G 18/10* (2006.01)
*C08G 18/12* (2006.01)

(52) U.S. Cl.
CPC ............ *A61K 31/785* (2013.01); *C08G 18/10* (2013.01); *C08G 18/12* (2013.01); *C08G 18/4277* (2013.01); *C08G 18/6484* (2013.01); *C08G 18/66* (2013.01); *C08G 18/6633* (2013.01); *C08G 18/6666* (2013.01); *C08G 18/755* (2013.01)

(58) Field of Classification Search
CPC .. A61K 31/785; C08G 18/4277; C08G 18/66; C08G 18/6484; C08G 18/6666; C08G 18/755; C08G 18/10; C08G 18/12; C08G 18/6633

See application file for complete search history.

(56) References Cited

FOREIGN PATENT DOCUMENTS

DE  19546371  * 12/1995  ............. C08G 18/10

OTHER PUBLICATIONS

English translation of DE 19546371, 2014, pp. 1-11. (Year: 2014).*

* cited by examiner

*Primary Examiner* — Trevor Love
(74) *Attorney, Agent, or Firm* — Patterson Intellectual Property Law, P.C.; Ryan D. Levy; Mark A. Kilgore

(57) ABSTRACT

The present disclosure relates to compositions A composition comprising a polymerization product of an anionic polysaccharide, a diisocyanate, and a linker, wherein the linker comprises i) an ether group, an ester group, or a combination thereof and, ii) a chain extender comprising a hydroxyl group, a thiol group, an amine group, or a combination thereof. The disclosure further relates to medical devices comprising the aforementioned compositions, and to methods of using the compositions and devices. More particularly, the compositions, devices and methods described herein are useful for preventing protein adhesions in vivo, particularly the Vroman effect.

20 Claims, 5 Drawing Sheets

Related U.S. Application Data

(60) Provisional application No. 61/544,260, filed on Oct. 6, 2011.

COPOLYMERS OF HYDROPHOBIC AND HYDROPHILIC SEGMENTS THAT REDUCE PROTEIN ADSORPTION

CROSS-REFERENCE TO RELATED APPLICATIONS

This application claims the benefit of priority of Provisional Application No. 61/544,260 filed on Oct. 6, 2011, and is a continuation of U.S. patent application Ser. No. 13/645,941, the contents of which are herein incorporated by reference in their entirety.

TECHNICAL FIELD

The present disclosure provides copolymers and compositions comprising the same, which are useful for reducing or preventing protein absorption in vivo, and more particularly, the Vroman effect.

BACKGROUND

The Vroman Effect is exhibited by protein adsorption to a surface by blood serum proteins. The highest mobility proteins generally arrive first and are later replaced by less motile proteins that have a higher affinity for the surface. A typical example of this occurs when fibrinogen displaces earlier adsorbed proteins on a biopolymer surface and is later replaced by high molecular weight kininogen. In surgical applications and wound healing, a generalized Vroman effect can be applied to all cellular/prosthetic interactions, wherein a foreign body is identified by the denaturation of proteins that attach to the implant surface, and thus label the implant as a foreign body and signal cells to wall off or removed by phagocytosis an implant. Similarly, cells traveling through the extracellular matrix of tissue proceed by laying down proteins from which they derive locomotion. Thus, an implant that prevents protein attachment prevents both labeling of an implant as a foreign body and colonization of the implant by fibrogenic cells and microbes.

Thus, controlling protein adsorption on implantable medical devices is important in controlling the foreign body response, the adverse form of which is chronic inflammation. Chronic inflammation leads to fibrotic encapsulation and the release of several factors that result in apoptosis and abundance of reactive oxygen species.

Biomaterials typically exhibit diverse protein adsorption, leading to mixed layers of partially denatured proteins. These surfaces contain different cell binding sites due to adsorption of proteins such as fibrinogen, immunoglobulin which results in attachment of inflammatory cells such as macrophages and neutrophils. When activated, these cells secret a wide variety of pro-inflammatory and proliferative factors. Hydrophilic surfaces control these events, and absorb little or no protein, primarily due to their dipole interactions with water. Unfortunately, hydrophilic substances generally possess poor volume stability and are susceptible to hydrolytic and enzymatic degradation.

Implants can generally be divided into two categories, those that are absorbable, and those that are intended to be biostable. For those implants that are bioabsorbable, it is important that the absorption rate is sufficiently slow to minimize inflammatory response and local changes in pH. Complete healing of a surgically altered site is widely believed to be about 6 months, if the patient has a normal healing response, for example adequate collagen production and blood supply. In cases where healing is compromised, a bioabsorbable implant may need to provide mechanical integrity for multiple years, while avoiding a foreign body response.

Accordingly, there is a need for a composition useful for medical devices that prevents protein adsorption while possessing volumetric stability and durability in vivo for a desired period of time. Such compositions would be expected to mitigate the foreign body response in vivo.

BRIEF SUMMARY

The present disclosure provides a composition comprising a polymerization product of an anionic polysaccharide, a diisocyanate, and a linker, wherein the linker comprises i) an ether group, an ester group, or a combination thereof and, ii) a chain extender comprising a hydroxyl group, a thiol group, an amine group, or a combination thereof. In certain embodiments, the polymerization product comprises a copolymer of a prepolymer and the linker, wherein the prepolymer comprises a copolymer of the anionic polysaccharide and the diisocyanate. The prepolymer comprises, in certain embodiments, at least one segment represented by I[BAB-BAB]nI, wherein, independently for each occurrence, A represents a polysaccharide block, B represents a urethane or urea block, I represents an isocyanate and n represents and integer ranging from 1 to 10,000. In certain embodiments, the linker comprises at least one segment represented by ECE, wherein, independently for each occurrence, C represents an ether block, an ester block or a combination thereof, and E represents a chain extender comprising a hydroxyl, a thiol or an amine group. Thus, the polymerization product may comprise at least one segment represented by [BAB-BAB]$_n$BCB[BABBAB]$_n$, wherein, independently for each occurrence, A represents a polysaccharide block, B represents a urea or urethane block, C represents an ether block, and ester block or a combination thereof, and n represents an integer ranging from 1 to 10,000.

In other embodiments, the polymerization product comprises a copolymer of a prepolymer and the anionic polysaccharide, wherein the prepolymer comprises a copolymer of the linker and the diisocyanate. In certain embodiments, the prepolymer comprises at least one segment represented by IBCBI, wherein C represents an ether block, an ester block, or a combination thereof. wherein the prepolymer comprises at least one segment represented by IBCBI, and wherein C represents an ether block, an ester block, or a combination thereof. Thus, when combined with a linker represented by ECE, the polymerization product comprises at least one segment represented by ABBCBBA, wherein independently for each occurrence, A represents a polysaccharide block, B represents a urea or urethane block, and C represents an ether block, an ester block, or a combination thereof.

The aforementioned polymerization products, in certain embodiments, thus comprise a polymer of one or more polyanionic polysaccharides and one or more non-absorbable ethers combined via urea or urethane links, which associate within the composition by hard segment bonding. More particularly, disclosed is a biocompatible composition (e.g. for coating or device) containing one or more polyanionic polysaccharides (e.g. hyaluronic acid, alginates, cellulose) combined with one or more hydrophilic non-absorbable ethers, the combination means comprising a urea or urethane link which associate within the composition by hard segment bonding.

In certain embodiments, the copolymers described herein are capable of reducing or preventing protein adsorption, and more particularly, the Vroman effect, in viva More particularly, in certain embodiments, the copolymers comprise hydrophobic and hydrophilic domains.

The disclosure also provides medical devices comprising a composition comprising a polymerization product of an anionic polysaccharide, a diisocyanate, and a linker, wherein the linker comprises i) an ether group, an ester group, or a combination thereof and, ii) a chain extender comprising a hydroxyl group, a thiol group, an amine group, or a combination thereof. The present disclosure further provides methods of reducing protein adsorption using the aforementioned medical devices in vivo.

The present disclosure further provides compositions comprising copolymers of hydrophilic domains and hydrophobic domains. In certain embodiments, the hydrophilic domains prevent protein adsorption, while the hydrophobic domains provide structural stability. The compositions of the disclosure can be provided in the form of an adhesion prevention composition, e.g., in a coating, membrane, foam, film, or composition suitable for extrusion. For example, the compositions can be extruded into fibers and knitted or weaved into a fabric. In particular embodiments, the composition comprises a water insoluble polysaccharide, and is produced in the form of fibers or fabric. In certain embodiments, the composition may also be provided in a prepolymeric form and then further copolymerized to form a device or coating for a device, for example, a coating for a mesh, such as polypropylene mesh, or copolymerized to form a film.

It is an object of the present disclosure to provide a polysaccharide polymerized with urea or urethane links subsequently reacted with ether or ester groups wherein at least two polysaccharide groups are connect by urea or urethane links.

It is another object of the present disclosure to provide a substance wherein the hydrophobic groups and hydrophilic groups of the non-saccharide segments are sized and distributed to mitigate against protein adhesion.

It is another object of the present disclosure to provide a substance that mitigates protein adhesion and promotes cellular infiltration, in particular the substance attracts cells responsible for neovascularization.

It is another object of the present disclosure to provide a substance that can be implanted in living tissue to promote healing of a wound which does not promote a strong foreign body response, does not result in a chronic inflammatory response, does not become thickly encapsulated with fibrotic, avascular tissue, and early in the healing process encourages vessel formation and infiltration of metabolic tissue.

It is another object of the present disclosure to provide an implantable coating that shields from living tissue a material that incites a strong foreign body response.

It is another object of the present disclosure to provide an implantable coating that temporarily shields from living tissue a material that incites a strong foreign body response, such that metabolic tissue can infiltrate the coated material prior to the coating being bioabsorbed.

It is another object of the present disclosure to provide a shielding coating to a structural soft tissue repair device, e.g., a surgical mesh.

It is another object of the present disclosure to provide a surgical barrier, one side of which blocks tissue adhesions and the other side of which promotes tissue adhesion and ingrowth.

It is another object of the present disclosure to provide a biocompatible material for forming absorbable fibers which can be woven, knitted, or otherwise constructed into mesh structure suitable for repair of soft tissue defects.

It is another object of the present disclosure to provide an absorbable polyurethane material which does not alter the local pH of the tissue environment in which the material resides.

It is another object of the present disclosure to provide an absorbable polyurethane material which swells when exposed to aqueous solutions, and thus is suitable for the uptake of therapeutic agents dissolved in water.

It is another object of the present disclosure to provide a superior hyaluronic acid structure comprised of segments of hyaluronic acid joined by urea or urethane links, said links modifying the hydrophilicity of the hyaluronic acid, and providing improved stability in a living tissue environment.

It is another object of the present disclosure to provide a superior hyaluronic acid structure comprised of segments of hyaluronic acid joined by urea or urethane links, said links modifying the hydrophilicity of the hyaluronic acid, and providing improved stability in a living tissue environment; and additionally said hyaluronic acid urea/urethane segment is joined to ether or ester segments, singly or in copolymer form. Said hyaluronic acid urea/urethane segments and said ether or ester segments randomly or periodically joined. Furthermore, the size and distribution of said hyaluronic acid urea/urethane segments and said ether or ester segments are chosen so as to mitigate protein adhesion.

It is another object of the present disclosure to introduce the notion of a generalized Vroman effect, which is responsible for identification of foreign objects in the body, and involves a series of protein adsorption and desorption on a foreign body, which when blocked or reduced renders an implant bio-transparent to the foreign body response. And it is an object of the present disclosure to provide a material that mitigates foreign body response by rendering an implant bio-transparent.

It is another object of the present disclosure to provide an implantable material that is devoid of collagen, but promotes neovascularization of a wound repair site and encourages the body to form its own collagen during the healing process which complements the formation of metabolic tissue.

It is another object of the present disclosure to provide a substitute to biologics, or any material derived from living tissue extracellular matrix devoid of antigenic material, such that it does not elicit a foreign body response due to the present of allograph collagen or the presence of crosslinks that alter the structure of living collagen and hyaluronic acid complexes.

It is another object of the present disclosure to provide a synthetic substitute to biologics which is suitable for used in failed or contaminated tissue repair sites.

It is another object of the present disclosure to provide a mesh, either coated or comprised of the material of the present disclosure, for use in pelvic floor repair where tissue adhesions are prevalent.

It is another object of the present disclosure to provide a polymer which resists microbial adhesion by mitigating the generalized Vroman effect.

Embodiments according to the current disclosure can be described as methods of making disclosure compositions. For instance, some disclosure methods comprise reacting prepolymers of the present disclosure on a mesh comprised of fibers such that the prepolymers polymerizes on said mesh fibers and thereby completely covers said fibers.

DETAILED DESCRIPTION

Figure 1:
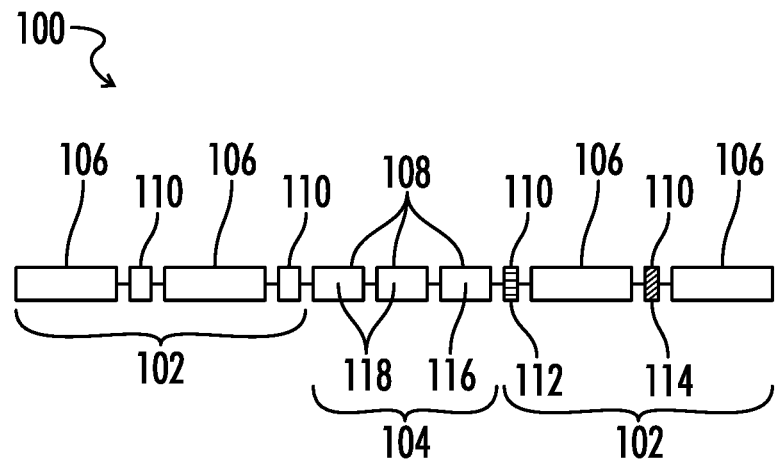
FIG. 1 illustrates domains of hydrophilic and hydrophobic zones in an embodiment of the copolymer of the present disclosure.

Provided herein is a biocompatible composition comprising a polymerization product of an anionic polysaccharide, a diisocyanate, and a linker, wherein the linker comprises i) an ether group, an ester group, or a combination thereof and, ii) a chain extender comprising a hydroxyl group, a thiol group, an amine group, or a combination thereof. In certain embodiments, the copolymers are capable of reducing or preventing protein adsorption, and more particularly, the Vroman effect when implanted in living tissue.

In certain embodiments, the polymerization product comprises a copolymer of a prepolymer and the linker, wherein the prepolymer comprises a copolymer of the anionic polysaccharide and the diisocyanate. For example, the prepolymer, may comprise anionic polysaccharide blocks A and urea or urethane blocks B, such that the prepolymer comprises at least one segment represented by ABBA, representing two polysaccharide blocks A joined by a diisocyanate such that two urethane or urea blocks B are produced. In further embodiments, the prepolymer includes at least one segment represented by I[BABBAB]$_n$I, independently for each occurrence, A represents a polysaccharide block, B represents a urethane or urea block, I represents an isocyanate and n represents an integer ranging from about 1 to about 10,000. Thus, the urethane or urea blocks B are derived from the reaction of the isocyanate groups of the diisocyanate with hydroxyl or amine groups on the anionic polysaccharide. In some embodiments, the polysaccharide blocks A are bound to a plurality of urethane or urea blocks B. For example, any desired number of free hydroxyl groups of the polysaccharide may be coupled to a diisocyanate, such that the polysaccharide blocks A are covalently bound to multiple urea or urethane blocks B. Such structures are further capable of providing cross-linked copolymers.

Thus, certain embodiments can be described as a composition comprising the polymerization product of a polymeric isocyanate said polymeric portion comprising anionic polysaccharide blocks A, urethane blocks B and isocyanate groups I with structure IBABBABI reacted with hydroxyl and amine chain extenders E containing an ether C, for example of the form ECE. Thus when reacted, IBABBABI and ECE form structures like IBABBABBCBBABBABI. These structures are differentiated functionally from polyol multi-isocyanates of the form IBCBI reacted with polysaccharides A, where the minimum form is ABBCBBA, and there is no occurrence of the sequence ABBA.

In certain embodiments, the linker comprises at least one segment represented by ECE, wherein, independently for each occurrence, C represents an ether block, an ester block or a combination thereof, and E represents a chain extender comprising a hydroxyl, thiol, or an amine group. Thus, upon reaction of a prepolymer represented by I[BABBAB]$_n$I, as described above, with a linker represented by ECE, the resulting polymerization product comprises at least one segment represented by [BABBAB]$_n$BCB[BABBAB]$_n$, wherein, independently for each occurrence, A represents a polysaccharide block, B represents a urea or urethane block, C represents an ether block, and ester block or a combination thereof, and n represents an integer ranging from 1 to 10,000. In certain embodiments, the [BABBAB] blocks are hydrophilic and absorbable relative to the [BCB] blocks. In alternative embodiments, a polymerization product comprises at least one segment represented by [BABBAB]$_n$[BC$_m$B]$_p$, wherein the [BABBAB] segments and [BC$_m$B] segments are randomly associated. In theses blocks, numerals m, n, p are integers from 1-10,000. The moieties consist of anionic polysaccharide blocks A, urethane blocks B and isocyanate groups I with structure IBABBABI reacted with hydroxyl J and amine K chain extenders E containing an ether or ester C, for example E is of the form JCJ or KEK. The C-moiety is preferably comprised of ether groups. Thus when reacted, IBABBABI and ECE form structures like IBABBABBCBBABBABI. These structures are novel in the occurrence of the sequence ABBA. Consequently, the compositions of the present invention have at least one segment as represented by the following formulas: ABBA, representing two polysaccharides A joined by a diisocyanate converted into two urethane links.

Accordingly, in certain embodiments when the copolymer of the prepolymer and the linker comprises at least one segment represented by [BABBAB]$_n$BCB[BABBAB]$_n$, the copolymer may comprise a linear structure, a cross-linked structure, or a mixture thereof. In certain embodiments, the copolymer is in a prepolymeric form, for example, further comprising one or more isocyanate groups. A non-limiting example of such a copolymer comprises at least one segment represented by I[BABBAB]$_n$BCB[BABBAB]$_n$I. Such prepolymeric forms may be further polymerized via urea or urethane linkages. In other embodiments, the isocyanate groups of the prepolymeric form may be end-capped by the reaction of the isocyanate group with water, an alcohol or an amine.

It is to be understood that the aforementioned polymeric segment encompasses structures in which the polysaccharide blocks A are covalently bound to a plurality of urea or urethane blocks B. For example, any desired number of free hydroxyl groups of the polysaccharide may be coupled to a desired number of diisocyanates, such that the polysaccharide blocks A are covalently bound to multiple polyurethane blocks B. The polyurethane blocks B optionally comprise an isocyanate. In embodiments wherein urethane linkages between the C block and the A block are desired, then the chain extender comprises a hydroxyl or thiol group. In embodiments wherein urea linkages are desired, the chain extender comprises an amino group.

In alternative embodiments, the polymerization product comprises a copolymer of a prepolymer and the anionic polysaccharide, wherein the prepolymer comprises a copolymer of the linker and the diisocyanate. In these embodiments, the prepolymer is derived from the reaction of the linker with the diisocyanate to produce a copolymer having at least one segment represented by IBCBI. Thus, the polymerization product of a linker represented by ECE and a prepolymer represented by IBCBI comprises at least one segment represented by ABBCBBA, wherein independently for each occurrence, A represents a polysaccharide block, B represents a urea or urethane block, and C represents an ether block, an ester block, or a combination thereof.

It is to be understood that the aforementioned polymeric segment ABBCBBA encompasses structures in which the polysaccharide blocks A are covalently bound to a plurality of urethane or urea blocks B. For example, any desired number of free hydroxyl groups of the polysaccharide may be coupled to a desired number of linkers of the form ECE, such that the polysaccharide blocks A are covalently bound to multiple C blocks via a urea or urethane. The polymerization product optionally comprises an isocyanate. In these embodiments, the copolymer may be further polymerized to produce cross-linked structures. Alternatively, the may be end-capped by the reaction of the isocyanate group with water, an alcohol or an amine.

In embodiments wherein urethane linkages between the C block and the A block are desired, then the chain extender comprises a hydroxyl or thiol group. In embodiments wherein urea linkages are desired, the chain extender comprises an amino group.

Examples of anionic polysaccharides useful in the present copolymers include, without limitation hyaluronic acid, glycosaminoglycans, aligantes, cellulose, carboxymethylcellulose, carboxymethylamylose, chondroitin-6-sulfate, dermatin sulfate, salts thereof and mixtures thereof. Accordingly, in some embodiments, the polysaccharide block A is derived from hyaluronic acid, glycosaminoglycans, aligantes, cellulose, carboxymethylcellulose, carboxymethylamylose, chondroitin-6-sulfate, dermatin sulfate, salts thereof and mixtures thereof. In certain embodiments, the anionic polysaccharide is hydrolytically labile, such as a hyaluronic acid or a salt thereof. As used herein the term "hyaluronic acid" refers to hyaluronic acid and any of its hyaluronate salts, including, for example, sodium hyaluronate, potassium hyaluronate, magnesium hyaluronate, and calcium hyaluronate.

Hyaluronic acid comprises repeating units of D-glucoronic acid and D-N-acetylglucosamine, both of which contain hydroxyl groups. Hyaluronic acid is a naturally occurring mucopolysaccharide found, for example, in synovial fluid, in vitreous humor, in blood vessel walls and umbilical cord, and in other connective tissues. The polysaccharide consists of alternating N-acetyl-D-glucosamine and D-glucuronic acid residues joined by alternating β 1-3 glucuronidic and β 1-4 glucosaminidic bonds. In water, hyaluronic acid dissolves to form a highly viscous fluid. The molecular weight of hyaluronic acid isolated from natural sources generally falls within the range of $5 \times 10^4$ up to $1 \times 10^7$ daltons.

Hyaluronic acid is an example of a glycosaminoglycan. Some of the useful properties of glycosaminoglycans are: a) they are negatively charged molecules, b) they possess an extended conformation that imparts high viscosity when in solution, c) they are located primarily on the surface of cells or in the extracellular matrix, d) they have low compressibility in solution and, as a result, are ideal as a physiological lubricating fluid, and e) their rigidity provides structural integrity to cells and provides passageways between cells, allowing for cell migration. The glycosaminoglycans of highest physiological importance are hyaluronan, chondroitin sulfate, heparin, heparan sulfate, dermatan sulfate, and keratan sulfate. Most glycosaminoglycans bind covalently to a proteoglycan core protein through specific oligosaccharide structures. Therefore, they are ideal structures for promoting healthy interface with extracellular matrix, and their combination with a polyurethane reduces the destructive cellular responses to foreign bodies.

Hyaluronic acid is readily soluble in water, but only sparingly soluble in organic solvents. Unfortunately, isocyanates are readily converted to amines in the presence of water. Thus, in order to react hyaluronic acid with an isocyanate in a manufacturing process, the hyaluronic acid can be made soluble in a non-aqueous solvent. For example, hyaluronic acid may be modified so that it is soluble in organic solvents to make practical most manufacturing processes. One of the modification methods is to modify hyaluronic acid with PEG and/or adding positive charge tridodecyl methyl ammonium chloride (TDMAC) to neutralize the negative charges of hyaluronic acid to make the hyaluronic acid soluble in an organic solvent. In certain embodiments, hyaluronic acid is modified with ammonia to render it soluble in organic solvent.

Isocyanates react with hydroxyl groups of the anionic polysaccharides to form urethane links. Thus, an anionic polysaccharide can be converted to a polyisocyanate upon the reaction with a diisocyanate. In some embodiments, all or most of the hydroxyl groups of the polysaccharide are reacted with the diisocyanate. For example, at least 75% of the hydroxyl group may be reacted with diisocyanate. In other embodiments, 75% to 100% of the hydroxyl groups are reacted with the diisocyanate, for example about 80%, 85%, 90%, 95%, 98 or 99% of the hydroxyl groups are reacted with the diisocyanate. Prepolymers of a polysaccharide, such as hyaluronic acid, and diisocyanate wherein most or all hydroxyl group is capped with diisocyanate are more stable in storage. By way of example, upon reaction of a diisocyanate with a hyaluronic acid, the hyaluronic acid is converted to a polyisocyanate. Hyaluronic polyisocyanates of the present disclosure may, in some embodiments, be comprised of multiply cross-linked hyaluronic acid blocks. These prepolymers may comprise some unreacted hydroxyl groups. In other embodiments, all or most of the hydroxyl groups are reacted with the diisocyanate. Similar structures comprising urea links instead of urethane links may be formed when the polysaccharide comprises amine groups.

In certain embodiments, the diisocyanates are aliphatic, cycloaliphatic or aromatic. Additionally, the diisocyanate may be selected such that its hydrolysis product is a biocompatible diamine. While not being bound by any particular theory, degradation by amine formation is contemplated to be hindered relative to hydrolytic degradation of the polysaccharide, thereby suppressing amine formation. Examples of diisocyanates useful for producing the B blocks of the copolymers of the present disclosure include without limitation 1,4-thisocyanatobutane, 1,2-diisocyanatoethane, lysine ester diisocyanate, 1,5-diisocyanatopentane, toluene diisocyanate, isophorone diisocyanate, or any combination of these.

In an embodiment, the prepolymer of the anionic polysaccharide (such as hyaluronic acid) and the diisocyanate is hydrophilic, and its hydrophilicity can be adjusted by the choice of diisocyanate. While not being bound by any particular theory, it is believed that the role of the urethane linkage in the prepolymers of the present disclosure is to stabilize the anionic polysaccharide segment (e.g. hyaluronic acid) against degradation in vivo.

The linker can be employed to further adjust the overall hydrophilicity of the reaction product, in some embodiments. Linkers are molecules comprising two or more chain extenders comprising functional groups, which are linked by a relatively stable chain. In certain embodiments, the functional groups are hydroxyls, thiols, amines, or combinations thereof. The unreactive portion of the chain extender may comprise ether groups, ester groups, or combinations thereof. In some embodiments, the chain comprises ether groups, such as ethylene oxides and propylene oxides.

Thus, in certain embodiments, the linker comprises at least one segment represented by ECE, wherein C represents an ether block, and ester block or a mixture thereof, and E represents a chain extender comprising a hydroxyl or an amine group. C may be ethylene oxide and/or propylene oxide copolymers. Additionally, C may be comprised of a hydroxyacid, a hydroxyacid composition, a hydroxyacid oligomer, an amino acid, an amino acid composition, or an amino acid oligomer.

In certain embodiments, C comprises ether blocks, such as a polyalkylene oxide. In particular embodiments, C represents a polyethylene oxide and polypropylene oxide (PEO/PPO) chain. Examples of PEO/PPO include commercially available PEO/PPO surfactants such as a Pluronics. In other embodiments, C is derived from polyols such as Multranol, or other polyethers, such as Tetrathane. In other embodiments, C comprises a hydroxyacid, such as a hydroxyacid oligomer or polymer.

Ethylene oxides are relatively hydrophilic and propylene oxides are relatively hydrophobic. The randomness and blockiness of ethylene oxide/propylene oxide copolymers can be used to achieve the overall Vroman modulation of the polymerized product. For example, the hydrophobicity can be employed to push water toward the hyaluronic acid block, making degradation of the hyaluronic acid segments more likely compared to degradation of the urethane links. In certain embodiments, the C block comprises ethylene oxide and propylene oxide monomers in a number ratio ranging from about 65:35 to about 85:15 ethylene oxide:propylene oxide. In other embodiments, the C block comprises ethylene oxide and propylene oxide monomers in a number ratio ranging from about 35:65 to about 15:85 ethylene oxide: propylene oxide. The stability and hydrophilicity of polyethers can, in certain embodiments, be modulated by the relative concentrations of propylene oxide and ethylene oxide blocks.

The C block also may comprise an ester, or an ester copolymerized with the above-discussed ethers, for example an ether-ester copolymer. The inclusion of an ester, in some embodiments, provides a degradable block within the C block. In certain embodiments, the ester comprises a hydroxy acid, such as 2-hydroxyacids, including lactic acid or glycolic acid, 3-hydroxy acids such as 3-hydroxybutyric acid, 3-hydroxyvaleric acid, 3-hydroxypropanoic acid, or 3-hydroxyhexanoic acid, 4-hydroxy acids, such as 4-hydroxybutyric acid, 4-hydroxy valeric acid, 4-hydroxyhexanoic acid; or ε-hydroxy-caproic acid.

Other esters that provide a degradable C block include polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures.

In certain embodiments, the C block further includes a urea or urethane linkage, and more particularly, a urethane linkage. For example, the C block can be derived from the product of a polyether and a diisocyanate, or a polyether, a polyester and a diisocyanate.

Some polyurethanes are both biostable and hydrophilic. Polyurethanes are not usually considered bioabsorbable polymers because they contain a hydrolytically stable urethane linkage. The stability can also be modulated by the addition of polysaccharides, which is a preferred degradation pathway over degradation of urethane blocks into amines. The stability of polyurethanes can be enhanced by crosslinking, the use of aromatic rather than aliphatic isocyanates, and the inclusion of degradable hydrophilic blocks. These degradable blocks can be made more biostable by juxtaposition of urethane links, modifying a hydrolytically unstable compound into one capable of persisting in living tissue for several months. Incorporating hydrolytically labile groups into the polymer backbone alters polyurethane biodegradability. Thus, in certain embodiments, compositions of varying stability in vivo can be produced.

In certain embodiments, the choice of urethane vs urea links between the prepolymers and the linker affect hydrophobicity of the polymerized product. Hydrophilic segments are created, for example, when polyoxyalkylene chains and hyaluronic acid chains are predominantly interconnected by urea links. In this embodiment, at least 50 percent of the individual oxyalkylene groups may be oxyethylene groups. Hydrophobic segments are created when polyoxyalkylene chains and hyaluronic acid chains are predominately interconnected by urethane links. In this embodiment, substantially all of the oxyalkene groups can be ethylene oxide.

In the production of urea links, diamines can be employed as chain extenders. Thus, in a linker comprising the segment ECE, E represents a chain extender comprising an amino group. These amines can be used to end-cap polyoxyalkylene chains or they may be used unaltered. Polyol C blocks can be amidated by reacting a polyol with di-, tri- or polyamino compounds. An example of a diamino compound useful in this embodiment is $NH_2CH_2CH_2(OCH_2CH_2)_nNH_2$, where n=2 to 12. Other diamino or polyamino compounds include; aliphatic di/tri/polyamines, such as; $H_2N(CH_2)_nNH_2$ wherein n=0 to 6, hydroxy-di/tri/polyamines, such as $H_2N(CH_2)_n(CHOH)_mNH_2$, wherein n=0 to 2 and m=0 to 2. Examples include 1,3-diamino-2-hydroxypropane, 1,3-diaminoacetone, 2,5-diaminobenzenesulfonic acid, 3,5-diaminobenzoic acid, 2,6-diaminopyridine, 2,5-diaminopyridine, 2,6-diaminopurine, 1,4-butanediamine, 1,2-ethanediamine, 1,5-pentanediamine; lysine ester, arginine ester and mixtures thereof.

In some embodiments, the chain extender comprises an alcohol-amine, a diamine, a diol, a dithiol, or any combination of these. The diamine can be selected from 1,4-butanediamine, lysine ester, 1,2-ethanediamine, arginine ethyl ester, 1,5-pentanediamine, or any combination of these. The diol can be selected from 1,3-propanediol, 1,2-propanediol, 1,4-butanediol, 1,6-hexanediol, 1,10-decanediol, cyclohexanedimethanol, and poly(caprolactone)diol, 1,5-pentanediol, 1,4-cyclohexanediol, 1,7-heptanediol, 1,8-octanediol, 1,9-nonanediol, 1,12-dodecanediol, poly(caprolactone) diol, or any combination of these. Chain extenders useful in the production of urethane links include 1,3-propanediol, 1,2-propanediol, 1,4-butanediol, 1,6-hexanediol, 1,10-decanediol, cyclohexanedimethanol, and poly(caprolactone)diol, 1,5-pentanediol, 1,4-cyclohexanediol, 1,7-heptanediol, 1,8-octanediol, 1,9-nonanediol, 1,12-dodecanediol, and caprolactone diol. Some embodiments specifically exclude anyone or any combination of these diols. The diols can be used to endcap the C blocks, for example, polyether blocks.

The isocyanate endcapping of the hydroxyl groups on the anionic polysaccharides of the present disclosure can be performed using solvents. Useful solvents are dimethylsulfoxide, dimethylacetamide, dimethylformamide, tetrahydrofuran, 1,4-dioxane, and methylene chloride. Anhydrous conditions are required as water consumes isocyanate groups. The isocyanate endcapping can also be catalyzed with tin salts such as tin (II) 2-ethylhexanoate and dibutyltin dilaurate.

In certain embodiments, the copolymers of the present disclosure are biodegradable. "Biodegradable" in the present disclosure means that a substance is not hydrolytically, oxidatively, or enzymatically stable, and is substantially broken down in an in vivo environment over a period of about 1 to about 60 months, or about 6 to about 24 months, or about 6 to about 12 months. For example, a biodegradable polymer is not hydrolytically, oxidatively, or enzymatically stable, and is substantially broken down by the in vivo in any of the aforementioned time periods. As used herein, "substantially broken down" means the mechanical or biologic functionality of the biodegradable substance is reduced by at least half. This can be confirmed by use of appropriate in vivo animal models, which allow the implant to be removed and analyzed at serial time points. A way of testing biodegradability is to immerse the substance in a solution that mimics the in vivo environment and monitor its mean molecular weight loss over time. If the material has lost more than 50% of its mean molecular weight over a 6-month period, then it can be characterized as biodegradable.

Depending upon the reaction sequence and/or relative reactivity of the monomers, invention polymers or compositions can be more random-like or more block-like. A polymeric composition C1 is more random-like than a polymeric composition C2 if the amount of information required to describe C1 is greater than the amount of information required to describe C2. For example, a polymeric composition comprised one type of repeating segments is less random than a polymeric composition comprised of two types of repeating segments, and a maximally random polymeric composition contains no repeating segments. A polymeric composition C1 is more block-like than a polymeric composition C2 if the mean size of segments comprised of the same moiety or monomers of C2 is greater than the mean size of segments comprised of the same moiety of C2.

If the particular discussion of a polymer is silent regarding polymer topology, that discussion encompasses embodiments with a polymer topology selected from all topologies, random-like topologies, block-like topologies, random topologies, block topologies, and topologies intermediate between random-like and block-like topologies. Moreover, in some embodiments the polymer is selected to exclude polymers with topologies selected from random-like, block-like, random, block, topologies intermediate between random-like and block-like, or any combination of these topologies.

For purposes of this disclosure, "Vroman modulation" means adjusting a polymer's randomness, blockiness, hydrophilicity, charge distribution, fractal dimension with respect to the distribution of hydrophilic/hydrophobic units, etc., in order to substantially decrease protein adsorption, the number of adherent macrophages and inflammatory cells, the degree of inflammatory cell activation, and the concentration of reactive oxygen species surrounding the implant. Preventing the generalized Vroman effect involves the formation of protein blocking hydrophilic domains around structural hydrophobic domains. In certain embodiments, the copolymers described herein comprise hydrophilic domains and hydrophobic domains, as depicted in FIG. 1. More particularly, the copolymers comprise protein-blocking hydrophilic domains and structural hydrophobic domains. FIG. 1 illustrates domains of hydrophilic 102 and hydrophobic 104 zones in a copolymer 100 of the present disclosure. There are two large-scale regions, the hydrophilic region 102 occupied by a polysaccharide 106 and the hydrophobic region occupied by an ether, ester, or copolymer of ether and ester 108. Within these large-scale regions are small-scale regions. In one instance, the small-scale regions are hydrophobic segments 110 comprised of urea or urethane bonds. In another instance, the small-scale regions are hydrophobic segments comprised of esters or ethers. Within the small-scale regions are micro-scale regions. In one instance, within the urea or urethane small-regions 110 is either an aliphatic group 112 or aromatic ring 114. The aliphatic micro-regions 112 are hydrophilic relative to the aromatic micro-regions 114, but compared to the hydrophilic small-scale regions, both are hydrophobic. Within the small-scale ether regions there are micro-scale hydrophilic regions 116 and hydrophobic regions 118. Examples of micro-scale hydrophilic regions are ethylene oxides or glycols. Examples are micro-scale hydrophobic regions are propylene oxides or glycols. The small-scale ester regions are generally more hydrophobic than the micro-scale ether regions. Among the ester moieties, there are variations in hydrophilicity that can be employed in the present multi-scale architecture.

For example, hyaluronic acid and polyethylene glycol are both highly hydrophilic, while on the other hand polypropylene and polyurethanes are hydrophobic. By combining these constituents, a biocompatible composition can be synthesized, which prevents protein attachment and possess volumetric stability and durability in the living tissue environment.

The structural stability of the polymers of the present disclosure in an implant environment are, in some embodiments, governed by crosslinks, which are easily formed in the instance of many polysaccharides because they comprise multiple hydroxyl groups. Thus, in certain embodiments, the copolymer is cross-linked. In certain embodiments, "cross-linked" means that a solid polymer is insoluble in solvents and thermally changes chemical composition (degrades) prior to entering a liquid state. Inn other embodiments, the copolymer is linear, or substantially linear. In general, the stability is enhanced by a greater proportion of hydrophobic groups, but these have the disadvantage of attracting protein adhesion, and consequently must be shielded by hydrophilic groups since mitigation of the generalized Vroman effect is desired in polymers of the present disclosure.

In other embodiments, greater structural durability can be achieved by the use of small-scale hydrophobic regions interspersed in the large-scale hydrophilic polysaccharide regions. While the polysaccharides tend to fill the regions between them with water molecules, the hydrophobic regions tend to associate by charge interactions. This is a preferred approach to achieving cohesiveness of a biopolymer compared to crosslinking, since such charge induced bonds are not structural.

Figure 2:
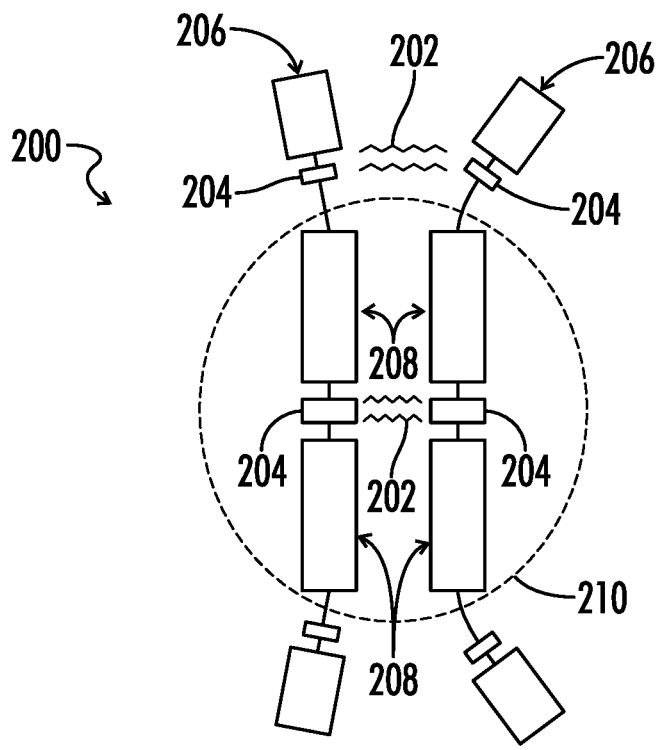
FIG. 2 illustrates the charge induced bonding between adjacent hard segment domains in polymer chains comprised of hyaluronic acid polymerized with urethane or urea links.

FIG. 2 illustrates the polymeric configuration due to charge induced bonding 200. The charge induced bonds 202 are induced between adjacent hard segment domains 204 in polymer chains 206 comprised of hyaluronic acid 208 polymerized with hard segment urethane or urea links. As illustrated, hydrophilic channels 210 comprised of hyaluronic acid are formed by aligning hydrophilic hyaluronic acid segments 208.

Figure 3:
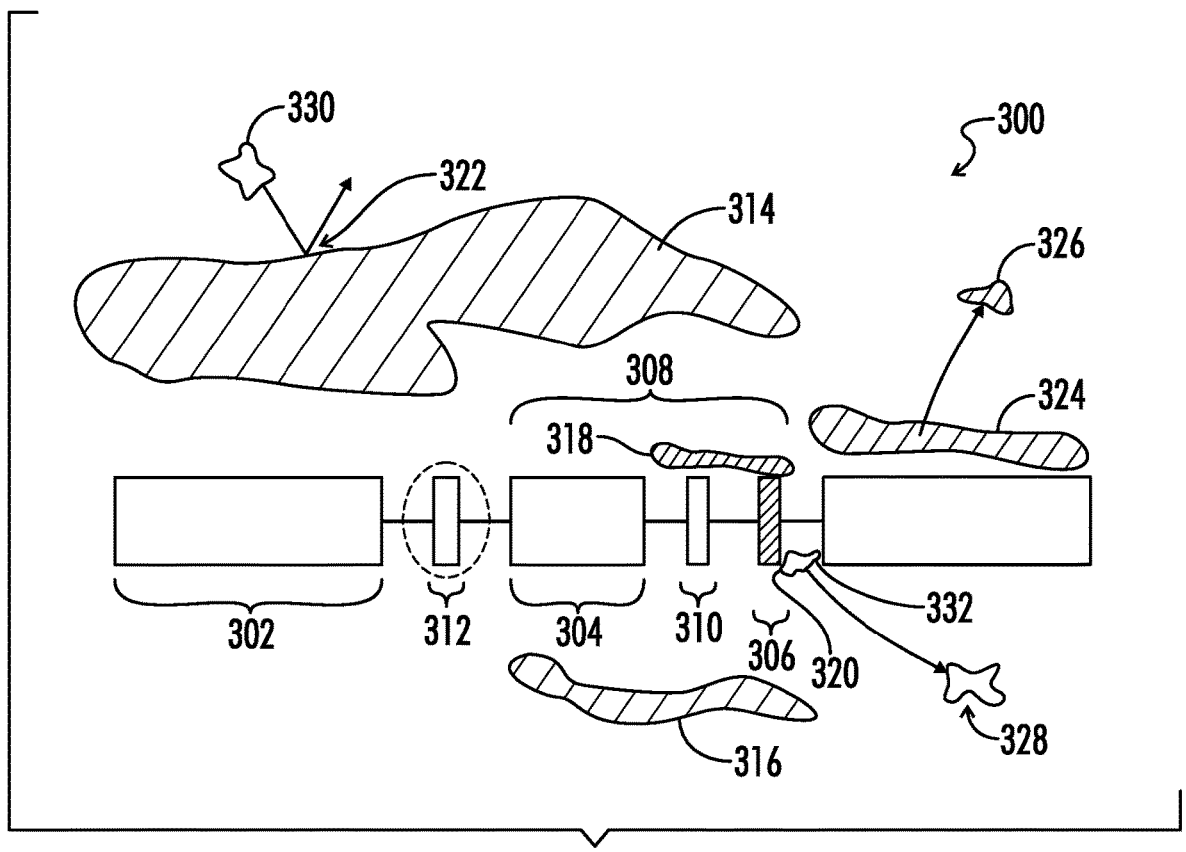
FIG. 3 illustrates the repulsion of proteins from an embodiment of a copolymer of the present disclosure.

Mitigation of the generalize Vroman effect involves blocking adhesion of protein to the polymer. FIG. 3 illustrates the repulsion of proteins from the polymer of the present invention 300. The polymer is comprised of large- 302, small- 304 and micro-scale 306 regions of hydrophilicity and large- 308, small- 310 and micro-scale 312 regions of hydrophobicity. The relative hydrophilicity is always compared to local domains of similar size, so in some cases a micro-scale hydrophilic region may be more hydrophobic than a distant micro-scale hydrophobic region. This is important since many proteins are small enough to be influenced by these micro-scale domains. Additionally, the overall degradation mechanism of the polymer, whether the implant degrades as visible flakes or molecular sized fragments depends on this multi-scale hierarchy. Once the shielding structure of hydrophilic segments juxtaposed with hydrophobic segments is disassembled, then mitigation of the generalized Vroman effect fails. So it is important to maintain this self-similar structure on many size scales, both to promote uniform and molecular level degradation as well as preserve the generalized Vroman mitigation even if a fragment should is associated due to stress in the implant environment. Consequently, the hydrophilic regions 302, 304, 306 are always juxtaposed to hydrophobic regions 308, 310, 312. However, it should be understood that the present invention intends to construct net large-scale hydrophobic regions and net large-scale hydrophilic regions, but their interaction with proteins, which are orders of magnitude smaller than cells, is intended to be mitigated by the small-scale balancing of hydrophobic and hydrophilic domains. A similar architecture resides at the micro-scale level relative to the small-scale level. Multi-scale hydrophobic/hydrophilic balancing at every level combined with distinct domain formation at the large-scale (cellular) level, preserves the protein blocking functionality while promoting the cell infiltrations functionality. And in particular, presents an architecture that promotes endothelial cell infiltration, the formation of new vessels, and the support of metabolic tissue.

Returning to FIG. 3, hydrophilic regions large-scale 302, small-scale 304, micro-scale 306 associate with water and create a water envelope 314, 316, 318, respectively. Water envelopes 314, 316, 318 shield the structural hydrophobic regions large-scale 308, small-scale 310, and micro-scale 312. When a microbe 330 (small- to micro-scale) or protein 332 (small- to micro-scale) attempts to attach to the polymer of the present invention 300 it may attach as in 320 or be repelled by stochastic processes as in 322. In the case where attachment occurs 320, water within the hydrophilic domain 324 is in exchange with the tissue environment and leaves the polymer surface 326 disrupting attached species 320 and sending it exterior to the polymer 328. The in-flux and out-flux of water, derived from the tissue, is responsible for the washing effect of the present polymer, and shields it from protein or microbial adhesion.

The present disclosure also provides medical devices comprising the compositions described herein. The devices are capable of preventing or reducing protein adsorption when placed in vivo, particularly the Vroman effect. More specifically, the devices comprise a composition that can prevent or at least reduce the build-up of a denatured layer of protein on its surface or on the device coating. In embodiment wherein the composition comprises hyaluronic acid, the hyaluronic acid blocks are released as the copolymer degrades in vivo, thereby directing cellular infiltration and neovascularization in the absence of the formation of inhibiting fibrosis, and additionally directing beneficial healing with metabolic tissue without the need for releasing pharmaceutically or therapeutically active agents. The compositions described herein can be cast into films or extruded into fibers, which can further be woven or knitted in to fabrics and used to form an implantable mesh. The devices and coatings can be prepared by allowing a prepolymeric form, which comprises isocyanate groups, to polymerize in the presence of water to form urea links. In other embodiments, the prepolymeric form can be polymerized under anhydrous conditions to form urethane links. In some embodiments, the devices described herein are absorbable in vivo, but do not substantially alter the local pH of the tissue environment in which the device is implanted.

In certain embodiments, the device is a mesh or a tissue scaffold comprising the aforementioned composition. In some embodiments, the mesh comprises a coating of the composition comprising any of the aforementioned polymerization products. For example, the mesh can be a polypropylene mesh comprising a coating of a composition of the present disclosure. In other embodiments, the mesh comprises fibers comprising the aforementioned composition. Such fibers can be prepared, for example, by extruding a composition described above. In certain embodiments, the mesh is a composite mesh, further comprising an anti-adhesive film. The meshes described herein are useful in soft tissue repair, wherein tissue adhesions are prevalent, such as pelvic floor surgeries.

In another embodiment, the device is a film comprising the composition described here. A film is prepared, in come embodiments, by allowing a prepolymeric form, which comprises isocyanate groups, to polymerize in the presence of water to form urea links. In other embodiments, the prepolymeric form can be polymerized under anhydrous conditions to form urethane links. In other embodiments, the device is a composite film comprising the film of the composition described herein coupled to an anti-adhesive film.

In certain embodiments, a composite device or coating may be formed of multiple layers. For example, a first layer may comprise a composition described herein, wherein the C block comprises all or mostly ether blocks, and a second layer may comprise a composition described herein wherein the C block comprises all or mostly ester blocks. In an embodiment, the device or coating comprises an inner layer comprising ether blocks and an outer layer comprising ester blocks. In these embodiments, the outer layer is absorbable while the inner layer is non-absorbable. In another embodiment, the inner layer comprises absorbable ester blocks and the outer layer comprises non-absorbable ether blocks. Thus, the inner layer is absorbable while the outer layer is non-absorbable.

In these or other embodiments, the medical device further comprises a therapeutic agent. The following types of therapeutic agents are found in some embodiments: proteins, peptides, antiproliferatives, antineoplastics, antiinflammatories, antiplatelets, anticoagulants, antifibrins, antithrombins, antimitotics, antibiotics, antioxidants, or their mixtures.

In certain embodiments, the implantable medical device is formed providing by number, molecular weight, and combinations of these, ratios of hydrophilic and hydrophobic domains that are self-similar on multiple size scales. In a further embodiment, an implantable medical device is formed by providing by number, molecular weight, and combinations of these, ratios of hydrophilic and hydrophobic domains that are self-similar on multiple size scales and possessing a fractal dimension of between 1.3 and 1.8.

The present disclosure further provides methods of reducing or preventing protein adhesions in vivo, and more particularly the Vroman effect, comprising providing a composition as described herein. The compositions may be administered to a subject in the form of the medical devices described above. In the present methods, the foreign body response to an implant is reduced or prevented. The present disclosure further provides a method of using combinations of hydrophobic and hydrophilic domains within an implantable copolymer to lessen the quantity of protein adhesion to the implant, such that the foreign body response of the tissue to said copolymer is reduced. In certain embodiments, the present methods increase the in situ durability of an absorbable polymer implant by placing hard segment urea or urethane links between absorbable segments in said polymer.

Capsule formation and remodeling of soft tissue repair prosthetics is responsible for reduced vascularization of a wound site. Vascularization of a wound site progresses by two mechanisms: sprouting and intussusception, the later occurring in resource starved environments. Sprouting angiogenesis begins with biological signals known as angiogenic growth factors that activate receptors present on endothelial cells present in pre-existing blood vessels. The activated endothelial cells begin to release enzymes called proteases that degrade the basement membrane to allow endothelial cells to escape from the original (parent) vessel walls. The endothelial cells then proliferate into the surrounding matrix and form solid sprouts connecting neighboring vessels. As sprouts extend toward the source of the angiogenic stimulus, endothelial cells migrate in tandem, using adhesion molecules, the equivalent of cellular grappling hooks, called integrins. These sprouts then form loops to become a full-fledged vessel lumen as cells migrate to the site of angiogenesis. Sprouting occurs at a rate of several millimeters per day, and enables new vessels to grow across gaps in the vasculature. Intussusception involves a capillary wall extending into the lumen to split a single vessel in two. The two opposing capillary walls establish a zone of contact. The endothelial cell junctions are reorganized and the vessel bilayer is perforated to allow growth factors and cells to penetrate into the lumen. A core is formed between the two new vessels at the zone of contact that is filled with pericytes and myofibroblasts. These cells begin laying collagen fibers into the core to provide an extracellular matrix for growth of the vessel lumen. Finally, the core is fleshed out with no alterations to the basic structure. Intussusception is important because it is a reorganization of existing cells. It allows a vast increase in the number of capillaries without a corresponding increase in the number of endothelial cells.

The deposition of collagen in association with the formation of new vessels is critical to vascularization of a wound site, and this structured collagen formation is performed in conjunction with cellular scaffolding. Thus the development of dense, disordered collagen (connective tissue) at a wound site serves an acute purpose of sealing, bridging and structurally buttressing a tissue defect. However this acute response blocks vascularization of the region. Furthermore, this type of collagen formation is sometimes called scarring, which is a confluent form of connective tissue characterized by contraction, loss of volume and mass. Therefore any neovascular that may form into the fibrous mass, and typically it does not, would be sheared off in the contracting mass, resulting in loss of blood flow and atrophy of the neovessels.

Figure 4:
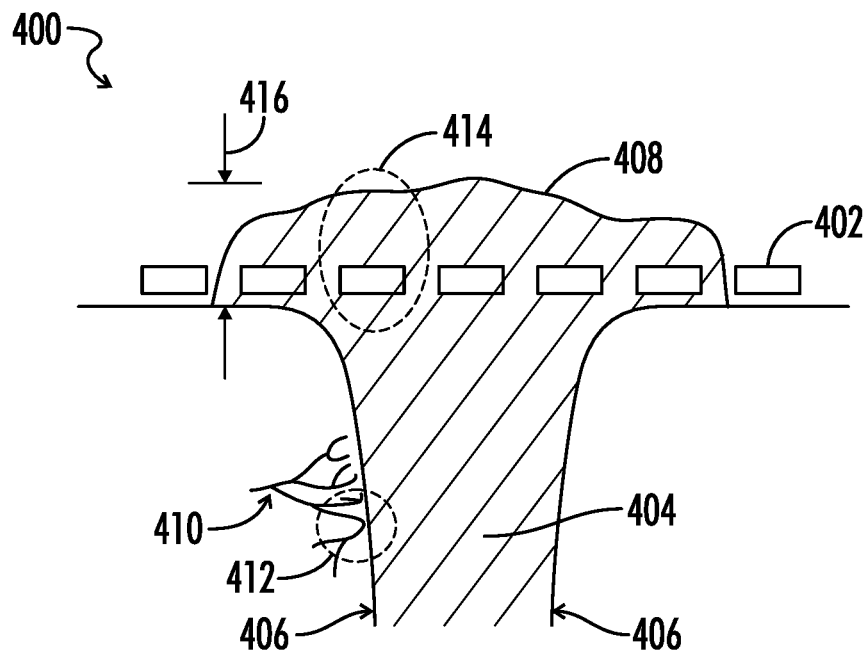
FIG. 4 illustrates the condition of chronic foreign body response in the situation of a synthetic mesh used to structurally support a wound site and the paucity of vessels in the region of healing.

FIG. 4 illustrates the condition of chronic foreign body response in the situation of a synthetic mesh used to structurally support a wound site and the paucity of vessels in the region of healing 400. Shown in cross section, a mesh 402 bridges a tissue defect 404 connecting wound edges 406. The material of the mesh 402 activates a strong foreign body response which results in the tissue defect 404 filling with dense, disorganized collagen 408. Sprouting vessels 410 are hindered in their effort to penetrate the living tissue/scar interface 412. Coincidentally, dense, disorganized collagen encapsulates 414 the mesh 402. Encapsulation 414 similarly blocks vessel infiltration. Furthermore, if the mesh 402 is particularly hydrophobic the thickness 416 of encapsulation 414 increases with time, further preventing neovascularization of mesh 402. Chronically, vascularization of the mesh 402 and tissue defect 404 is hindered by confluence or contraction of the established disordered collagen.

Figure 5:
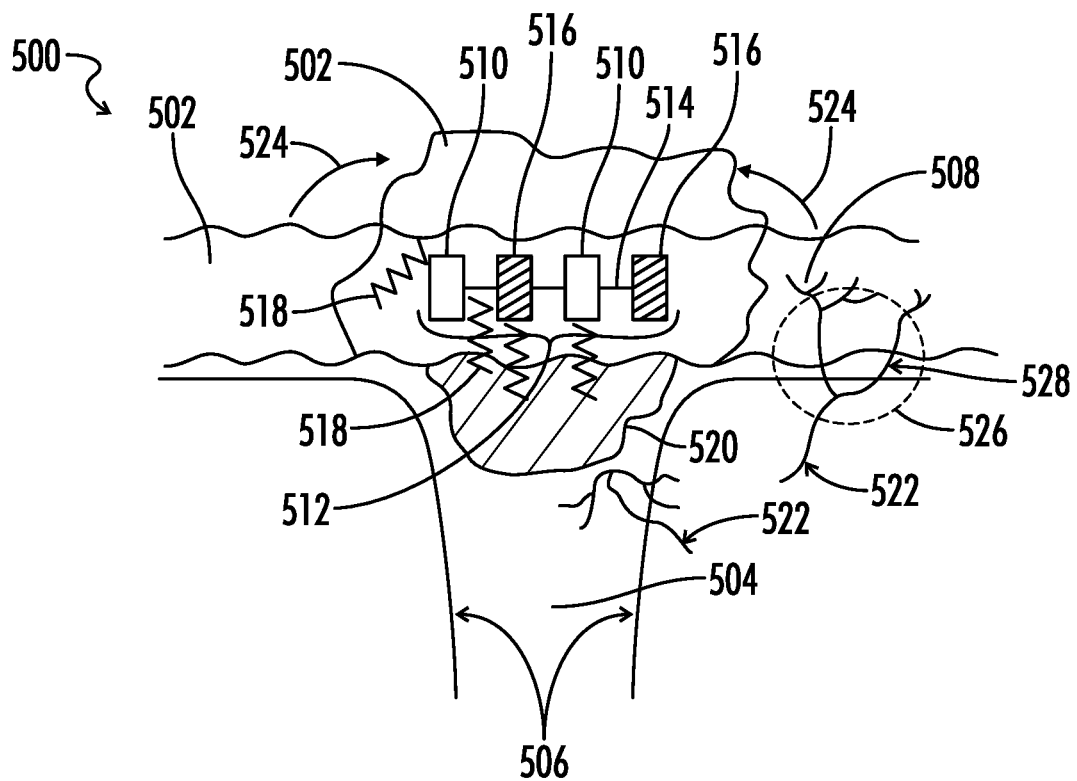
FIG. 5 illustrates the condition of chronic foreign body response in the situation of a biologic material used to structurally support a wound site and the effect on vascularity as the wound site remodels resulting in a paucity of vessels in the region of healing.

FIG. 5 illustrates the condition of chronic foreign body response in the situation of a biologic material used to structurally support a wound site and the effect on vascularity as the wound site remodels resulting in a paucity of vessels in the region of healing 500. Shown in cross section, a biologic 502 bridges a tissue defect 504 connecting wound edges 506. One of the anticipated benefits of biologics 502 is that they retain the extracellular matrix of the biological structure from which they were harvested. While these structures do promote angiogenesis 508 into the biologic material 502, pre-existing collagen 510 in the extracellular matrix 512 or artificial crosslinks 514 formed between collagen 510 and hyaluronic acid 516 comprising extracellular matrix 512 in the biologic 502 provides for protein attachment 518, which then signals a foreign body response resulting in deposition of disordered collagen 520 which blocks or reduces the density of neovascularization 522. The resulting inflammatory response contributes to degradation of the mesh and subsequent biologic contraction 524. The interface 526 between biologic 502 and Wound edges 506 is disrupted by contraction 524 shearing off or occluding 528 neovascularization 522.

Figure 6:
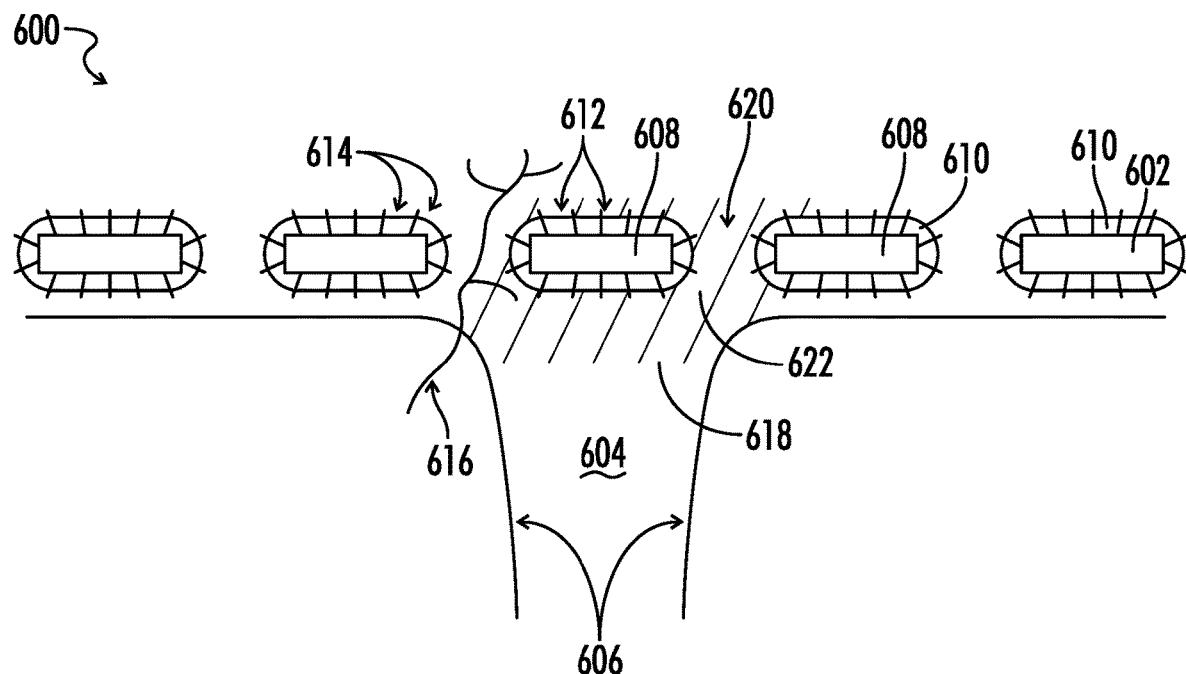
FIG. 6 illustrates the condition of healing using the present disclosure wherein the wound site is structurally intact and vascularized.

FIG. 6 illustrates the condition of healing using the present disclosure wherein the wound site is structurally intact and vascularized 600. Shown in cross section, a coated mesh of the present disclosure 602 bridges a tissue defect 604 connecting wound edges 606. The mesh is comprised of polypropylene fiber 608 coated with hyaluronic acid polyurethane 610. The coating 610 is comprised generally of hydrophobic structural segments 612 and hydrophilic protein blocking segments 614. The mechanism for protein blocking is illustrated in FIG. 3. The hyaluronic acid residing in the hydrophilic segments 614 promotes neovascularization 616. The absence of allograph collagen, and more generally protein attachment sites, is responsible for a reduced foreign body response and the deposition of disorder collagen. Therefore, the neovascularization 616 results in ordered collagen deposition 618 which serves to bridge the porous structure 620 and resulting in metabolic tissue 622 incorporating coated mesh 602. Metabolic tissue 622 is stable since it is not perceived as scar tissue, and thus is not remodeled. After metabolic tissue 622 incorporates coated mesh 602 the need for coating 610 is removed, and beneficially resorbs into the body. The structural element 608 remains, which is beneficial in maintaining the structural stability of the wound site, which can be subject to reherniation as disordered collagen 624 formed in tissue defect 604 is remodeled. This stability of the wound site promotes healthy revascularization of tissue defect 604.

Figure 7:
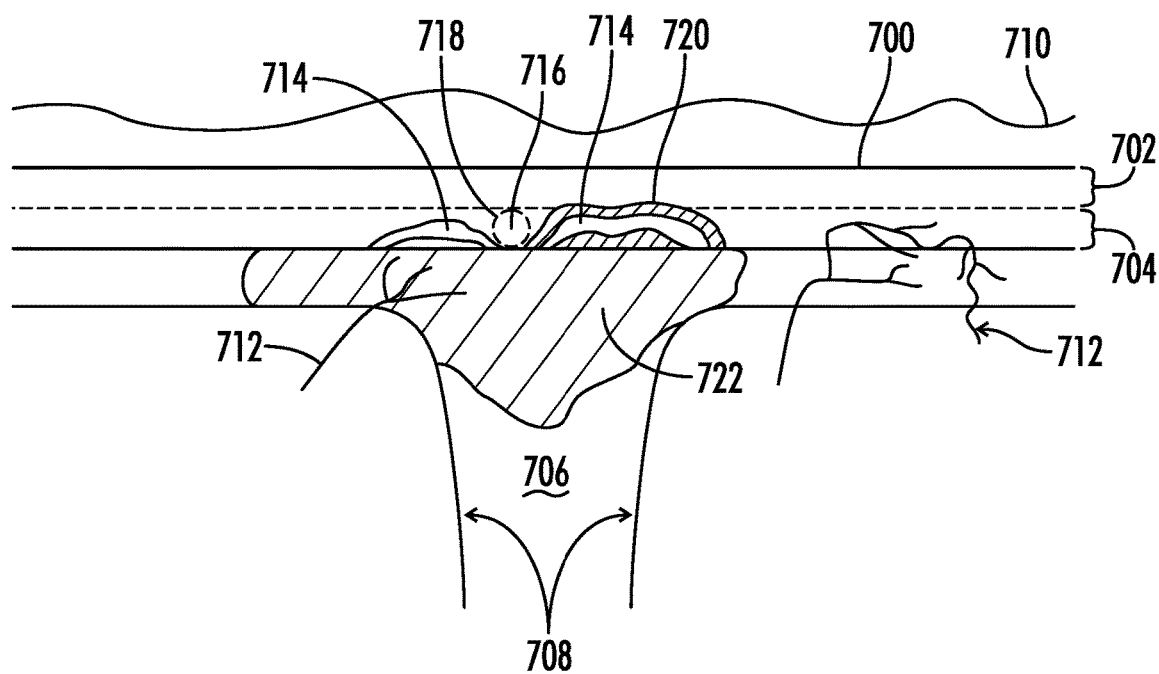
FIG. 7 illustrates a surgical adhesion barrier comprised of an anti-adhesive side and a tissue reparative side.

FIG. 7 illustrates a surgical adhesion barrier 700 comprised of an anti-adhesive side 702 and a tissue reparative side 704. The anti-adhesion side may be any of known anti-adhesion devices, e.g., polylactic acid, copolymers of hyaluronic acid and cellulose, polytetrafluoroethane, etc. The anti-adhesive side 702 preferably takes longer to absorb than the reparative side 704 or is not absorbable. Depicted in cross section is the adhesion barrier 700 in contact with a tissue defect 706 and defect edges 708. Anti-adhesive side 702 prevents the establishment of connective tissue between adjacent tissue layer 710 and defect edges 708. The reparative side 704 promotes ingrowth and vascularization 712 by providing a rapidly degrading component 714 and a persistent component 716 which form macroscopic hydrophobic 718 and hydrophilic 720 domains. The hydrophilic domains 720 resorb first attracting cellular infiltration and providing porosity for ingrowth and vascularization. Prior to implant resorption and loss of structural integrity a network of living cells and vasculature 722 bridges defect edges 708. This architecture further supports revascularization of tissue defect 706.

Figure 8:
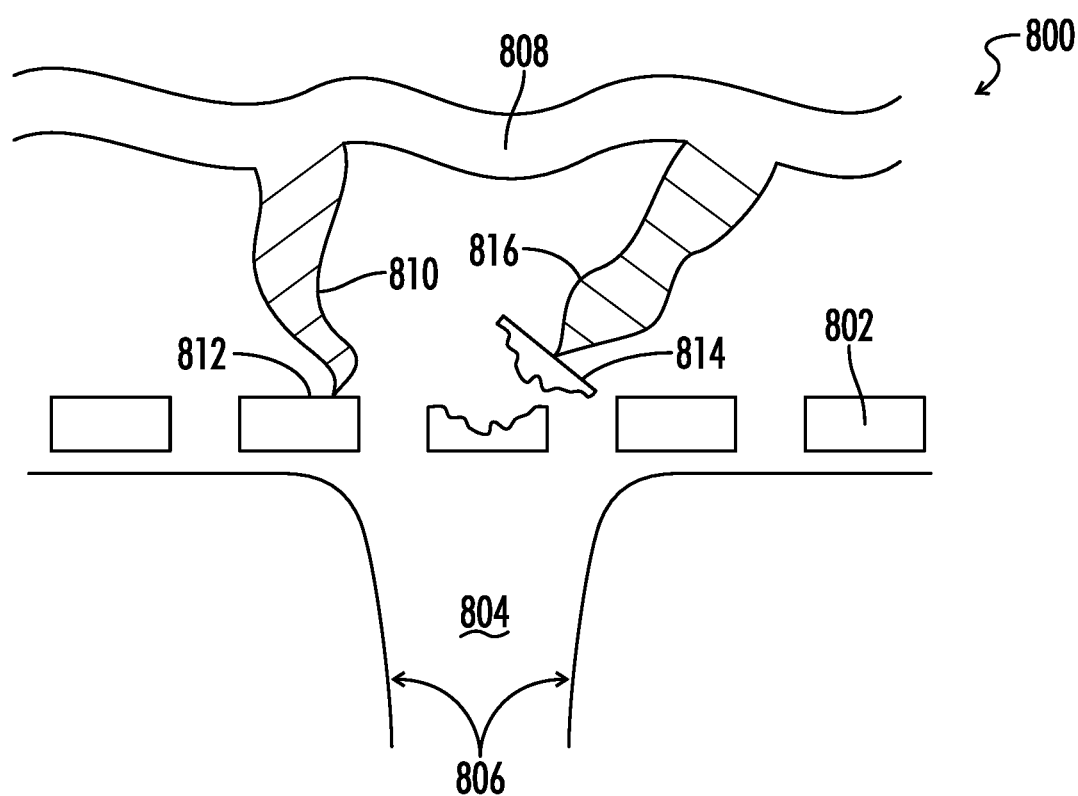
FIG. 8 illustrates an absorbable surgical mesh comprised of the present polymer, and the anti-adhesive functionality, and the ingrowth functionality.

FIG. 8 illustrates in cross section 800 an absorbable surgical mesh 802 comprised of the present polymer, and the anti-adhesive functionality, and the ingrowth functionality. By not evoking a strong foreign body response the collagen deposition necessary for adhesion formation is less prevalent. While generally, mesh 802 will not block adhesions as reliably as a film construct, it will form fewer and weaker adhesions compared to an uncoated permanent mesh. Adhesions that form may subsequently be released as mesh 802 degrades. Shown is a tissue defect 804, defect edges 806, and adjacent tissue layer 808. If adhesion 810 attaches at mesh surface 812, mesh molecules 814 eventually resorb causing adhesion 810 to detach from the mesh 816. The ingrowth functionality is similar to that described in FIG. 3 for a coated mesh construct.

Figure 9:
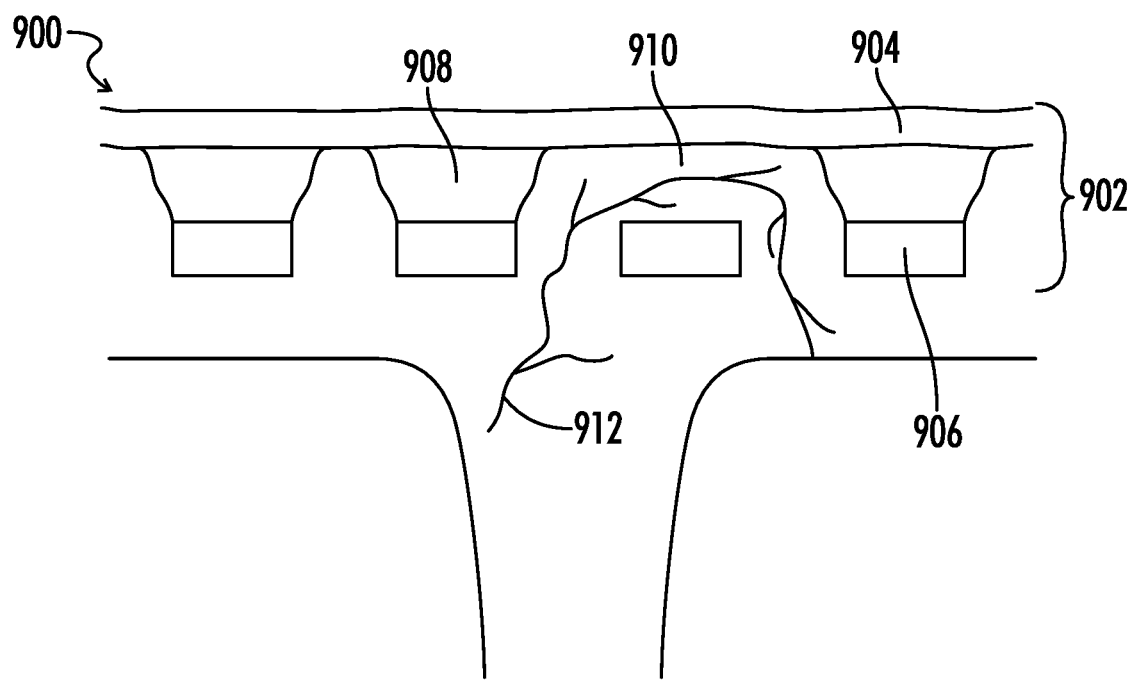
FIG. 9 illustrates a composite surgical mesh comprised of an anti-adhesion film coupled to a mesh coated with the polymer of the present disclosure.

FIG. 9 illustrates in cross section 900 a composite surgical mesh 902 comprised of an anti-adhesion film 904 coupled to a mesh 906 coated with the polymer of the present disclosure. The coating may function to join anti-adhesion film 904 to mesh 906. As coating 908 degrades as illustrated at location 910 a gap is formed through which vascularized tissue 912 may grow. Preferably, mesh 906 is substantially ingrown with vascularized tissue 912 prior to loss of functionality of the anti-adhesion film 904.

Additional embodiments of the present disclosure are listed below. It is another object of the present disclosure to provide a substance wherein the hydrophobic groups and hydrophilic groups of the non-saccharide segments are sized and distributed to mitigate against protein adhesion.

In certain embodiments, the compositions described herein mitigate protein adhesion and promotes cellular infiltration, in particular the substance attracts cells responsible for neovascularization. In certain embodiments, the compositions described herein can be implanted in living tissue to promote healing of a wound which does not promote a strong foreign body response, while preventing a chronic inflammatory response. Furthermore, the compositions, in certain embodiments, do not become thickly encapsulated with fibrotic, avascular tissue, and early in the healing process encourages vessel formation and infiltration of metabolic tissue.

In other embodiments, the present disclosure provides an implantable coating that shields from living tissue a material that incites a strong foreign body response. Additional embodiments, of the present disclosure provide an implantable coating that temporarily shields from living tissue a material that incites a strong foreign body response, such that metabolic tissue can infiltrate the coated material prior to the coating being bioabsorbed.

Further embodiments provide a shielding coating to a structural soft tissue repair device, e.g., a surgical mesh. Other embodiments provide a surgical barrier, one side of which blocks tissue adhesions and the other side of which promotes tissue adhesion and ingrowth. In another embodiment, a biocompatible material is provided for forming absorbable fibers which can be woven, knitted, or otherwise constructed into mesh structure suitable for repair of soft tissue defects.

In other embodiments, the compositions described herein comprise an absorbable polyurethane material, which does not alter the local pH of the tissue environment in which the material resides. The polyurethane material, in certain embodiments, swells when exposed to aqueous solutions, and thus is suitable for the uptake of therapeutic agents dissolved in water.

In another embodiment, the composition described herein comprises segments of hyaluronic acid joined by urea or urethane links, said links modifying the hydrophilicity of the hyaluronic acid, and providing improved stability in a living tissue environment; and additionally said hyaluronic acid urea/urethane segments are joined to ether or ester segments, singly or in copolymer form. The hyaluronic acid urea/urethane segments and said ether or ester segments can be randomly or periodically joined. Furthermore, the size and distribution of said hyaluronic acid urea/urethane segments and said ether or ester segments are chosen so as to mitigate protein adhesion.

It is another object of the present disclosure to reduce or prevent the Vroman effect. When the Vroman effect is blocked, an implant is rendered biotransparent to the foreign body response. Thus, the compositions herein, in certain embodiments, render medical devices, such as implant materials, biotransparent.

In other embodiments, the compositions described above are free from collagen. The compositions, in these embodiments, can promote neovascularization of a wound repair site and encourages the formation of endogenous collagen during the healing process.

In other embodiments, the disclosure provides methods of making the present compositions and devices. For instance, the methods can comprise reacting prepolymers of the present disclosure on a mesh comprised of fibers such that the prepolymers polymerizes on said mesh fibers and thereby coats said fibers.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified in any range. Any reference to a range should be considered as providing support for any subset within that range.

EXAMPLES

Examples are provided to illustrate some embodiments of the compositions and devices of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the examples. The source of chemicals employed in these examples is Sigma-Aldrich (Milwaukee, Wis.) unless otherwise noted.

Example 1: Polyethylene Oxide/Polypropylene Oxide Copolymers

Water soluble tri-block copolymers of polyethylene oxide (PEO) and polypropylene oxide (PPO) are commercially available non-ionic macromolecular surface active agents. Variation of the copolymer composition (PPO/PEO ratio) and molecular weight (PEO and PPO block lengths) during synthesis leads to the production of molecules with differing properties. Unfortunately, commercially available forms employ block structures that are typically larger than desired in certain embodiments of the present disclosure.

Since PEO is more reactive than PPO, fine scale block structures cannot be formed by merely placing the ratio amounts of PEO and PPO together in a reactor. Alternating segments of PEO and PPO can be synthesized by the sequential addition of first propylene oxide (PO) and then ethylene oxide (EO). These oxyalkylation steps are carried out in the presence of an alkaline catalyst, for example, sodium or potassium hydroxide. The catalyst is then neutralized and removed from the final product. By alternating additions of EO and PO one can make copolymers of particular PPO/PEO composition while varying the molecular weight of the PPO blocks. Thus a complete grid of copolymers are realizable, the grid comprised of constant PPO/PEO composition on the vertical axis and constant PPO block molecular weight on the horizontal axis.

Example 2: Hyaluronan Isocyanate

Hyaluronan is comprised of repeating segments of $C_{14}H_{21}NO_{11}$, each containing 5 hydroxyl groups (OH). To form a diisocyanate of hyaluronan one reacts a quantity of diisocyanate containing 2 moles of NCO greater than the number of moles of OH. Thus, for a hyaluronan containing 1 unit of $C_{14}H_{21}NO_{11}$ per molecule, 1 mole of hyaluronan molecules is to be reacted with 7 moles of diisocyanate. The reaction is performed in an organic solvent, where the hyaluronan is altered by ammonia to make it soluble in an organic solvent, such as tetrahydrofuran. A small amount of tin catalyst is added to promote urethane link formation between the hydroxyls of the hyaluronan and the isocyanate groups of the diisocyanate. To discourage chain extension, the hyaluronan is first dissolved in organic solvent and set aside. The reactor is charged with catalyst and diisocyanate and heated to 80 degrees C. The hyaluronan solution is slowly added to the reactor and the exotherm monitored. Complete reaction is indicated when the exotherm subsides. Alternatively, one can measure the % NCO at each step to verify all the hydroxyl groups on the hyaluronan are endcapped with isocyanate.

When all the hyaluronan is added to the reactor the reaction is run until the desired % NCO is reached. % NCO is measured by conventionally by dibutylamine titration. The reaction is complete when 2 moles of NCO are measured for every mole of product molecule. Ideally there is only 1 $C_{14}H_{21}NO_{11}$ unit per product molecule. However, in other applications a spectrum of product molecules containing a range of $C_{14}H_{21}NO_{11}$ unit per product molecule is desired. The desired polydispersity can be obtained by adjusting the amount of NCO used, and verifying with GPC and % NCO measurements. In any one reaction, the dispersity of molecular weights of product molecules will be Gaussian around a desired mean. Multi-modal distributions can be obtained by mixing the reaction product of multiple reactions. Hyaluronan isocyanates of higher isocyanate functionality can be synthesized by adjusting the ratio of OH groups to isocyanate groups in the reaction mix.

Example 3: Hyaluronan Polyurethane

A polyalkylene copolymer of PPO and PEO is synthesized according to EXAMPLE 1, wherein the PEO blocks contain 3 propylene oxide units, the PPO blocks contain 1 ethylene oxide unit, and these PEO and PPO blocks alternate, wherein the first block is a PEO and the last block is a PPO. The number of functional OH groups per molecule is approximately 2. A hyaluronan diisocyanate is synthesized according to EXAMPLE 2 wherein the molecular weight of the hyaluronan diisocyanate is approximately 3 times the molecular weight of the polyalkylene copolymer.

If the polyalkylene component or the hyaluronan diisocyanate components are not in liquid form at a reaction temperature of approximately 80 degrees C., then these components are dissolved in an organic solvent devoid of OH groups. The reactor is charged with 1 mole of hyaluronan diisocyanate and heated to 80 degrees C. The polalkylene copolymer is added slowly, waiting for the exotherm to subside after each addition.

If a prepolymeric form is desired, e.g., a reaction product that will polymerize on a mesh, then the component amounts are chosen to result in 2 moles of NCO per product molecule. Chains of arbitrary length of hyaluronan and polyalkylene can be synthesized by choosing the amount of isocyanate such that 2 moles of NCO remain per desired molecular weight of product molecule. In some cases, a prepolymeric form with 3 or higher isocyanate functionality per product molecule is desired, so that when polymerized on a medical device, the coating is cross-linked. Cross-linking of the polymer provides a coating that is more resistant to solvents or heat. Not every molecule must have higher functionality to obtain a polymerization product that is cross-linked.

If a linear polymer is desired, wherein the reaction product can be dissolved in solvent and solution cast, or melted and extruded, then some of the hyaluronan diisocyanate may be endcapped with a mono-functional alcohol such as ethanol. The molecular weight of the reaction product is selected by the ratio of diisocyanate to mono-isocyanate hyaluronan in the reaction mix. Alternatively, the chain extension can be terminated in reaction by adding ethanol to the reaction mix when the desired molecular weight is obtained. In this instance an excess of ethanol can be used, which is driven off by evaporation when all the NCO groups are consumed.

Dibutylamine titration can be used to determine when a reaction is done. In particular, in the polymer case, the reaction is complete when all NCO groups are consumed. In the prepolymeric case, the reaction is complete when the NCO number per product molecule reaches a desired value. In the case of crosslinking prepolymers the NCO number is greater than 2 per product molecule. In the case of non-crosslinking prepolymeric forms the NCO number equals 2 per product molecule.

The product molecules and polymerized forms are characterized by possessing in number ratio approximately 3 segments of hyaluronan per segment of polyalkylene. The polyalkyelene segment comprises in number ratio approximately 3 segments of ethylene oxide per segment of propylene oxide. The hyaluronan segment is more hydrophilic than the polyalkylene segment. The ethylene oxide segment is more hydrophilic than the propylene oxide segment. The urethane links between hyaluronan units having a molecular weight ratio of urethane to hyaluronan approximately the same as the molecular weight ratio of urethane to polyalkylene segments. The urethane links are more hydrophobic than the hyaluronan units or polyalkylene segments, the density of which can be tailored to form hard segment association between urethane links within the bulk volume of the polymer.

Example 4: Coated Polypropylene Mesh

An absorbable coating is formed on a conventional polypropylene mesh by dissolving a prepolymer of EXAMPLE 3 in an organic solvent. Preferably the organic solvent is devoid of OH groups, for example, acetone. The mesh can be coated by any number of techniques known in the industry. The mesh may be dipped, sprayed, brushed or otherwise coated with the prepolymers. Subsequent to coating, the mesh coating is allowed to polymerized by reaction with water in the atmosphere, thereby polymerizing by urea formation. Alternative difunctional polyols can be added to the prepolymer. In this case, the prepolymer will have a finite shelf-life and the molecular weight of the prepolymers solution will change as a function of time. When the mesh is coated, the polymerization can be forced by the addition of a catalyst, which can later be washed off. In this case, polymerization occurs by the formation of urethane links. If urethane links alone are desired, the polymerization phase must be carried out in a water-free atmosphere.

Example 5: Absorbable Mesh

Fibers of the polymers of EXAMPLE 3 can be made by heating to melt the polymer and extruding in fiber form. This fiber can be used to weave or knit mesh structures.

Example 6: Anti-Adhesion Film

A film can be made of the polymers and prepolymers of EXAMPLE 3. In the case where the prepolymer is used, the prepolymer is poured on a glass surface and allowed to polymerize with water in the atmosphere. Alternatively the prepolymer is mixed with a diamine and poured on a glass surface to form urea links. In yet another embodiment, the prepolymer is mixed with a diol and catalyst to form urethane links. In other embodiments, the prepolymer is mixed with a triol or higher functional polyol and catalyst. In the case where polymer is used, the polymer is dissolved in solvent or melted and poured on a glass surface.

Example 7: Composite Mesh

In this embodiment a mesh is coupled with a film. The mesh may be a conventional mesh or an absorbable mesh of EXAMPLE 5. The film may be a conventional anti-adhesion film, or a film of EXAMPLE 6. The mesh and film are coupled by clipping the mesh in a prepolymer of EXAMPLE 3. The film and coated mesh are brought into physical contact, optionally under pressure, such that as the prepolymer coating polymerizes, it links film to mesh. Multiple combinations of mesh and film are anticipated.

Example 8: Sheets of Hyaluronic acid/polyurethane (HA-PU) for In Vivo Studies

A triol (Multranol 9199) comprised of a copolymer of ethylene oxide and propylene oxide was obtained from Bayer HealthCare, Tarrytown, N.Y. In to a sealed, heated reactor was placed 455 g (0.1 moles) of Multranol. The Multranol was heated to 85° C. while stirring, and a vacuum applied to the reaction volume. This was continued until the water content of the Multranol was less than 300 ppm. The water content was measured using a standard Karl-Fischer setup. To the Multranol was added 52.2 g (0.3 moles.) of toluene diisocyanate (Sigma-Aldrich) in 10 g increments taking care to monitor any exothermic raise in temperature, and delaying additional additions until the temperature of the reaction volume remained constant (within 1° C.) for 5 minutes. While stirring, the temperature of the reaction volume was raised at 4° C. per minute until a temperature of 75° C. The reaction was continued until the % NCO was 2.5%. To this product, 40 g Hyaluronan of approximately 40,000 Dalton molecular weight (0.001 moles, Purity Products) was added in solution of 500 ml tetrahydrofuran (Sigma-Aldrich). The mixture was stirred until the hyaluronan was dissolved. The hyaluronan solution was added in 10 ml increments to the heated prepolymer volume (above). The head space of the reactor was filled with flowing nitrogen to take up the tetrahydrofuran that flashes off as the hyaluronan solution is added. Once the entire volume of the hyaluronan solution is added to the prepolymer, the mixture is heated for an additional 12 hours. Subsequently, a vacuum is applied to the reaction product while stirring and heating until all the volatiles in the reaction volume are removed. The above hyaluronan-polyurethane prepolymer can be mixed with water to form a polymerizing volume which can be cast in sheets. The weight ratio of water to prepolymer can be 50:50 to about 95:5.

Example 9

In this example, the in vivo performance of a surgical barrier layer (HA-PU sheets) comprised of a 75:25 ratio of water to prepolymer of Example 8 was tested. The tissue response to these HA-PU sheets was compared to polypropylene mesh. Cells of interest in the study of foreign body response were identified with Trichrome staining, and with H & E staining. Rats were used in assessing differences in foreign body response. Rats respond to foreign bodies with an exaggerated walling off response, so their fibrogenic response is elevated compared to humans. One difficulty in working with rats is their propensity to reopen wounds, infecting the wound site, and compromising a healthy foreign body response with infection. For this reason it is important to place the test article dorsally. Coated mesh constructs tend to curl when hydrated. This morphological change can induce a foreign body response, form gaps in the implantation site which additionally tends to fill in with fibrotic material. Therefore, it is important to well-localize the implant, minimize its size, and implant as deeply as practical. Dorsal implantation was applied left and right, of 2 one centimeter square test articles to be localized with four sutures placed at the corners. Ideally the test articles are hydrated in saline before implantation. It is important that the surgical incision be closed with care to avoid reopening. It is important that left and right pockets not be communicating. It is important that any chemicals used to sterilize the site, such as butadiene, not come in contact with the test article, since the proposed test articles will take up chemicals readily and these chemicals will change their foreign body response profile.

In Summary:
10, 1×1 cm uncoated mesh, packaged individually, sterilized
10, 1×1 cm films, packaged individually, sterilized at MAST
10 rats, each to receive 1 mesh and 1 film.
Implanted dorsally, left and right
Harvested at 7 days, placed in formalin
Stained Trichrome
Results:
Numerical values of counts normalized, N=10.
Mesh Vs HA-PU Sheet

|  | Uncoated Mesh | HA-PU Sheet | Significance |
| --- | --- | --- | --- |
| Fibrosis [mm] | 0.21 ± .07 | 0.015 ± 0.009 | $P < 0.001$ |
| Giant Cells | 1.53 ± 0.39 | 0.01 ± 0.005 | $P < 0.005$ |
| Eosinophils | 1.99 ± 0.51 | 0.09 ± 0.02 | $P < 0.0001$ |
| PMNs | 0.81 ± 0.24 | 0.19 ± 0.05 | $P < 0.01$ |
| Histiocytes | 2.53 ± 0.81 | 0.55 ± 0.17 | $P < 0.0005$ |
| Lymphocytes | 1.63 ± 0.41 | 0.10 ± 0.01 | $P < 0.01$ |

Example 10: Absorbable Pre-Polymer of Hyaluronan and Polyurethane

A linear, absorbable diol was synthesized. The chemical used in this example were obtained from Science Lab. Synthesis comprised 4 g of Terathane 2000 and 4 g of polycaprolactone diol (Mn=2000) placed into a 3-neck-flask. Toluene was added and then a part of the toluene was removed by distillation to get a 20% solution. After cooling to room temperature 4.05 g of isophorone diisocyanate were added under nitrogen. 0.37 g of DBTL (Dibutyltin dilaurate) was added and the mixture was heated to 75° C. After 5 hours 1.28 g of 1,4-butane diol were added and the reaction mixture was diluted with toluene to get concentration of all components of 15%. The temperature was raised to 80° C. After 10 hours the mixture was allowed to cool to room temperature. The resulting polymer is precipitated in pentane and dried in vacuo. The mechanical characteristics are: Elongation at break: 990% Tensile strength: 21 MPa Degradation: The material was subjected to an accelerated hydrolytic degradation experiment (2N caustic soda solution at 70° C.). After 4 days the molecular weight was reduced from 200 kDa to 19 kDa and the shape of the samples had changed. The material was so week that a mechanical characterization was not possible.

In to a sealed, heated reactor was placed 569 g (0.01 moles) of the above linear polymer with 500 ml acetone. The volume was mixed until the solid polymer was completely dissolved. To the above mixture was added 5.2 g (0.03 moles.) of toluene diisocyanate (Sigma-Aldrich) in 1 g increments taking care to monitor any exothermic raise in temperature, and delaying additional additions until the temperature of the reaction volume remained constant (within 1° C.) for 5 minutes. While stirring, the temperature of the reaction volume was raised at 4° C. per minute until a temperature of 75° C. The reaction was continued for 8 hours. To this product, 4.0 g Hyaluronan of approximately 40,000 Dalton molecular weight (0.0001 moles, Purity Products) was added in solution of 500 ml tetrahydrofuran (Sigma-Aldrich). The mixture was stirred until the hyaluronan was dissolved.

The hyaluronan solution was added in 10 ml increments to the heated prepolymer volume (above). The head space of the reactor was filled with flowing nitrogen to take up the tetrahydrofuran that flashes off as the hyaluronan solution is added. Once the entire volume of the hyaluronan solution is added to the prepolymer, the mixture is heated for an additional 12 hours. Subsequently, a vacuum is applied to the reaction product while stirring and heating until all the volatiles in the reaction volume are removed. Acetone is added to maintain a mixable volume. The resulting polymer can be solution cast on glass plate, allowing the acetone to evaporate.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A composition comprising a polymerization product of a prepolymer and a linker,
wherein the prepolymer is represented by I[BABBAB]$_n$I, wherein, independently for each occurrence, A represents a glycosaminoglycan block, or a salt thereof, each occurrence of B represents a single urethane or urea linkage derived from the reaction of a free hydroxy group of a glycosaminoglycan molecule, or a salt thereof, of the glycosaminoglycan block, with an isocyanate group of an aliphatic diisocyanate molecule, such that BB is formed from the reaction of both isocyanate groups on a single aliphatic diisocyanate molecule, I represents an unreacted isocyanate from an aliphatic diisocyanate, and n represents an integer ranging from 1 to 10,000,
wherein the linker comprises the structure ECE, wherein, independently for each occurrence, C represents an ether-ester copolymer block, the ether-ester copolymer block including a urethane linkage, wherein the ether-ester copolymer block is derived from the product of a polyether connected to a polyester via a diisocyanate and E represents the chain extender comprising a terminal hydroxyl, thiol, or amino group, wherein the terminal hydroxyl, thiol, or amino groups react with the unreacted isocyanates of the prepolymer to produce the polymerization product.

2. The composition of claim 1, wherein the polymerization product comprises at least one segment represented by [BABBAB]IBCB[BABBAB]n.

3. The composition of claim 2, wherein the polymerization product further comprises at least one isocyanate group.

4. The composition of claim 1, wherein the polymerization product comprises at least one segment represented by ABBCBBA.

5. The composition of claim 1, wherein the polymerization product comprises cross-links formed by the reaction of more than two diisocyanate molecules with more than two hydroxyl groups on the glycosaminoglycan block, or salt thereof.

6. The composition of claim 1, wherein the polyether comprises ethylene oxide and propylene oxide monomers.

7. The composition of claim 6, wherein the number ratio of ethylene oxide monomers to propylene oxide monomers ranges from about 65:35 to about 85:15.

8. The composition of claim 6, wherein the number ratio of ethylene oxide monomers to propylene oxide monomers ranges from about 35:65 to about 15:85 ethylene oxide: propylene oxide.

9. The composition of claim 7, wherein the hyaluronic acid block and ether have a weight ratio ranging from about 85:15 to about 65:35.

10. The composition of claim 8, wherein the hyaluronic acid block and ether have a weight ratio ranging from about 35:65 to about 15:85.

11. The composition of claim 1, wherein the polyester comprises a hydroxyacid.

12. A medical device comprising a composition comprising the composition of claim 1.

13. The medical device of claim 12, wherein the device is a mesh comprising the composition.

14. The medical device of claim 12, wherein the device is a mesh coated with the composition.

15. The medical device of claim 13, wherein the mesh comprises fibers comprising the composition.

16. The medical device of claim 13, wherein the mesh is coupled to an anti-adhesive film.

17. The medical device of claim 12, wherein the device is an implantable medical device coated with the composition.

18. The medical device of claim 12, wherein the device is a film comprising the composition.

19. The medical device of claim 12, wherein the device is a composite film comprising an anti-adhesion film coupled to a film comprising the composition.

20. A method for reducing protein adsorption to a medical device in vivo, comprising providing a medical device comprising the composition of claim 1.

* * * * *